(12) United States Patent
Hirose et al.

(10) Patent No.: US 11,642,091 B2
(45) Date of Patent: May 9, 2023

(54) X-RAY FLUOROSCOPIC IMAGING APPARATUS

(71) Applicant: SHIMADZU CORPORATION, Kyoto (JP)

(72) Inventors: Dai Hirose, Kyoto (JP); Koki Yoshida, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 101 days.

(21) Appl. No.: 17/493,593

(22) Filed: Oct. 4, 2021

(65) Prior Publication Data

US 2022/0167937 A1 Jun. 2, 2022

(30) Foreign Application Priority Data

Nov. 27, 2020 (JP) .............................. JP2020-197561

(51) Int. Cl.
*A61B 6/00* (2006.01)
*A61B 6/04* (2006.01)

(52) U.S. Cl.
CPC ............ *A61B 6/487* (2013.01); *A61B 6/0407* (2013.01); *A61B 6/4441* (2013.01); *A61B 6/4452* (2013.01); *A61B 6/461* (2013.01); *A61B 6/54* (2013.01)

(58) Field of Classification Search
CPC ... A61B 6/0407; A61B 6/4441; A61B 6/4452; A61B 6/461; A61B 6/487; A61B 6/54
See application file for complete search history.

(56) References Cited

U.S. PATENT DOCUMENTS

2019/0388044 A1* 12/2019 Hirose ................... A61B 6/487

FOREIGN PATENT DOCUMENTS

| JP | 2019-193875 A | 11/2019 |
|---|---|---|
| JP | 2020-081410 A | 6/2020 |

* cited by examiner

*Primary Examiner* — Dani Fox
(74) *Attorney, Agent, or Firm* — Andrew F. Young, Esq.; Nolte Lackenbach Siegel

(57) ABSTRACT

An X-ray fluoroscopy imaging apparatus has a plurality of imaging equipment component members including an X-ray source, an X-ray detector, a C-arm, a table and a display unit; a input receiving element, an information element; and a control element that controls the information element to inform that the second imaging equipment component member moves when controlling the move of the first imaging equipment component member among a plurality of imaging equipment component members and moving the second imaging equipment component member while interlocked with the move of the first imaging equipment component member.

10 Claims, 11 Drawing Sheets

Second Alternative Embodiment

Schematic lateral plane view of subject

Schematic plane view from feet side of subject

FIG. 5
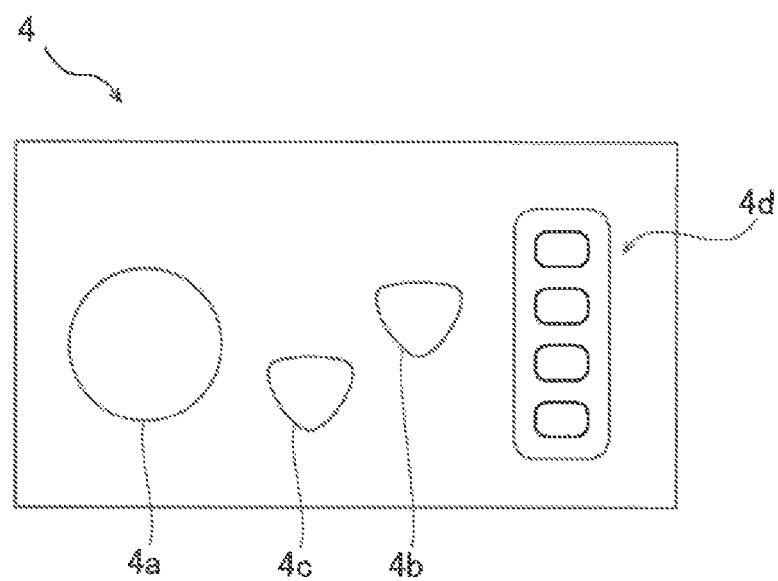
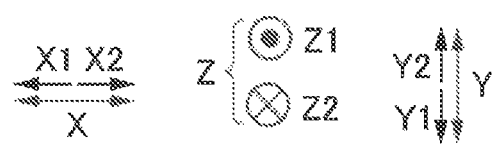

*FIG. 6*
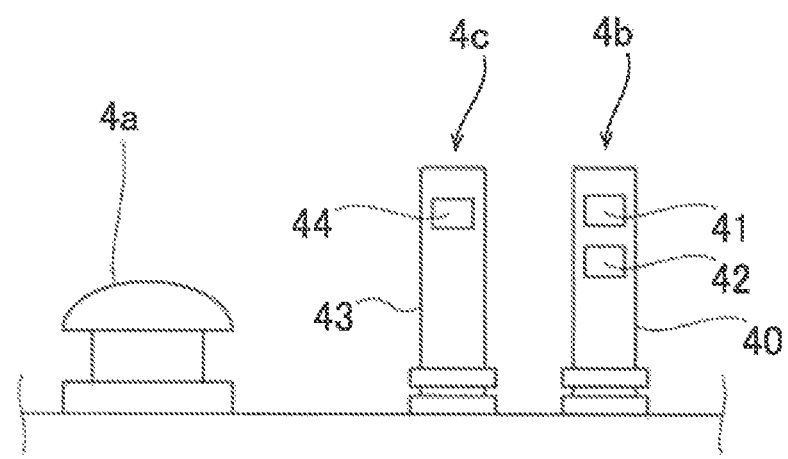
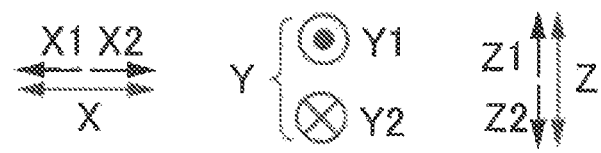

FIG. 7A  Start moving Table
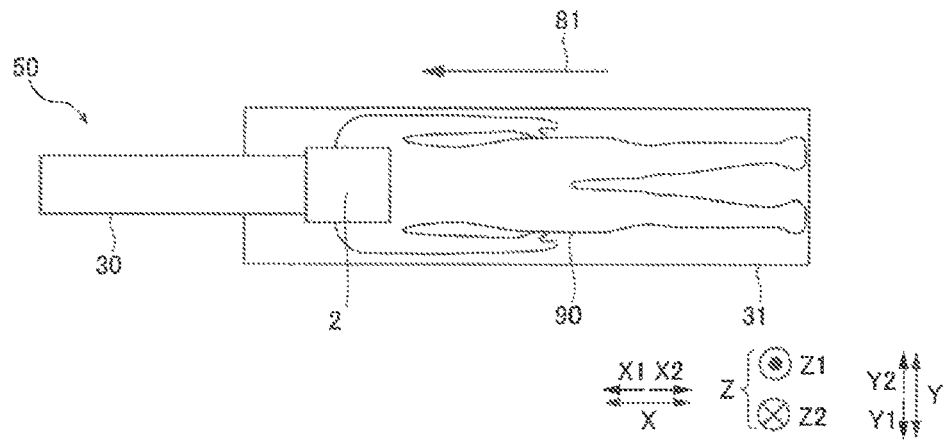
FIG. 7B  Turning C-arm
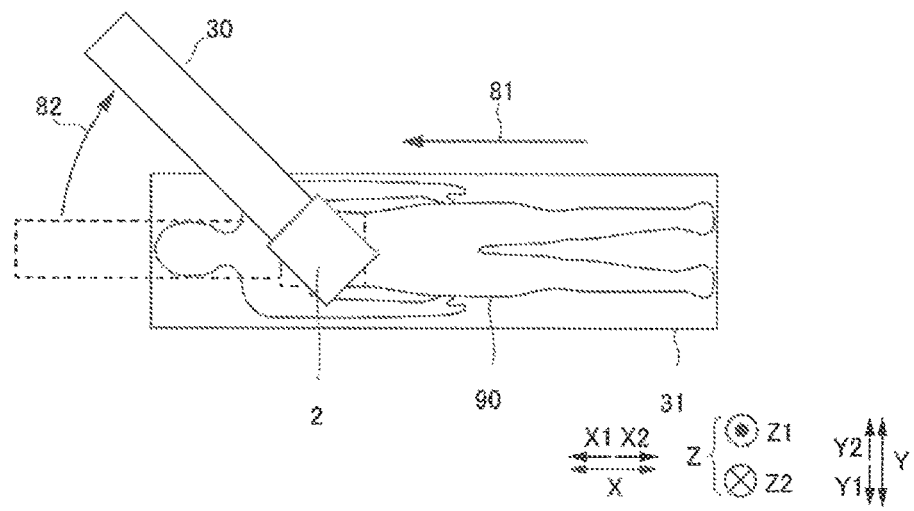
FIG. 7C  Move Table to position of lower leg to be imaged
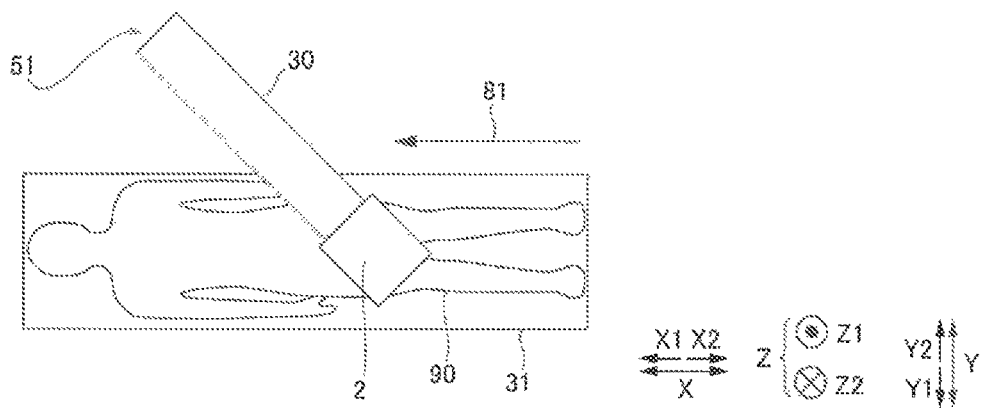

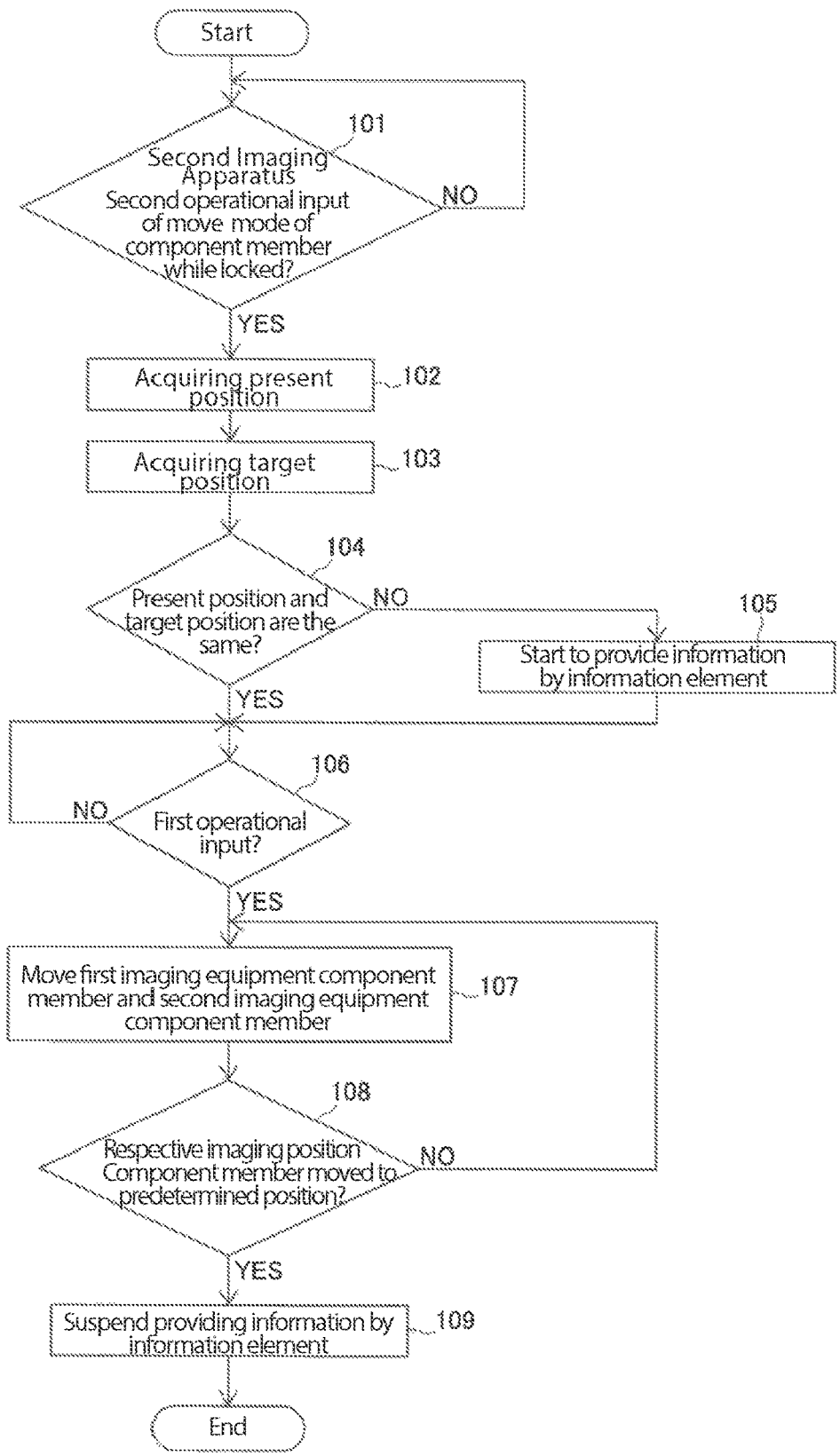
FIG. 8  Move processing of Imaging Equipment Component Member

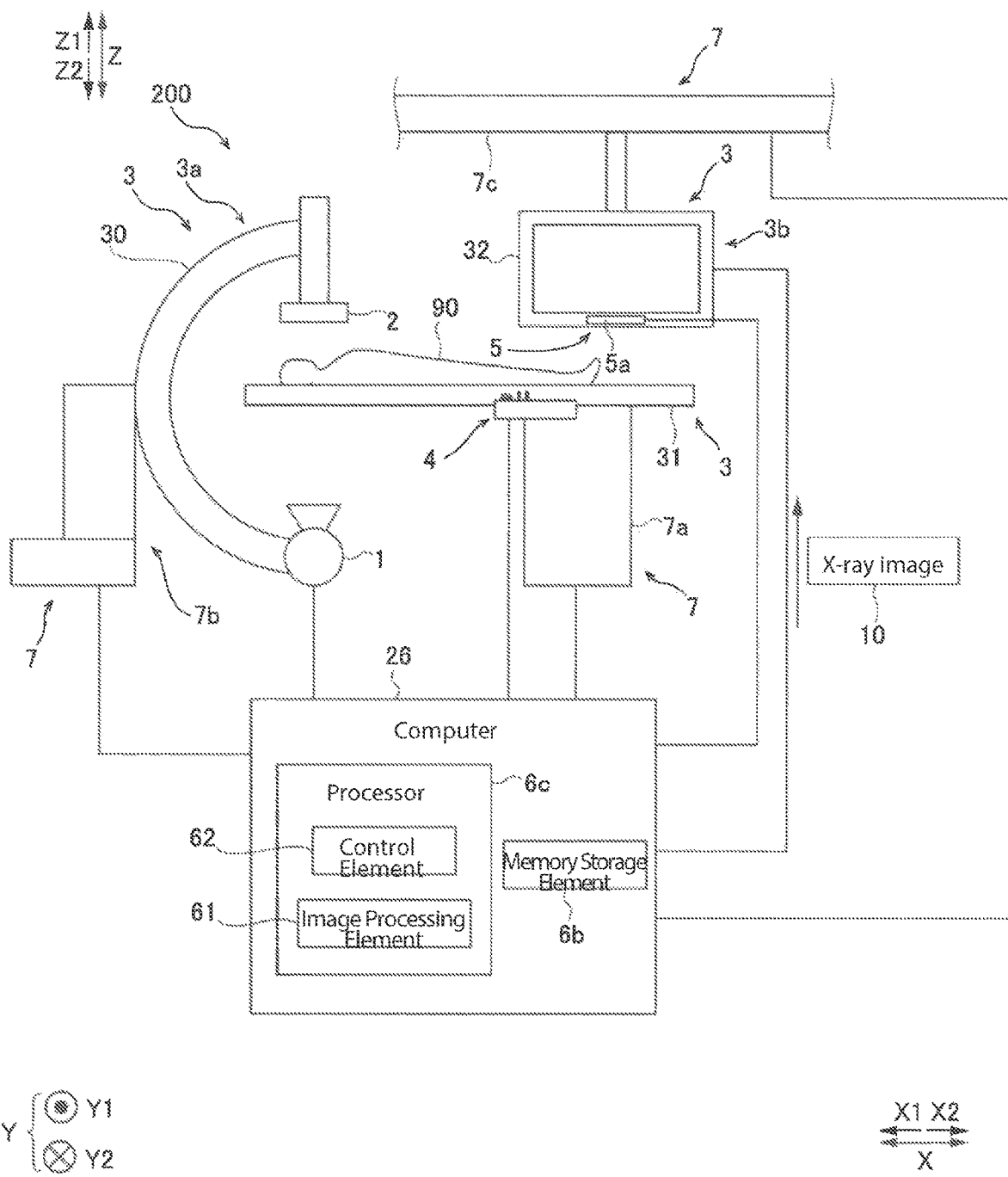
FIG. 9  First Alternative Embodiment

First Alternative Embodiment
Start turning of C-arm

First Alternative Embodiment
Retreat display element

First Alternative Embodiment
Turn C-arm until predetermined position

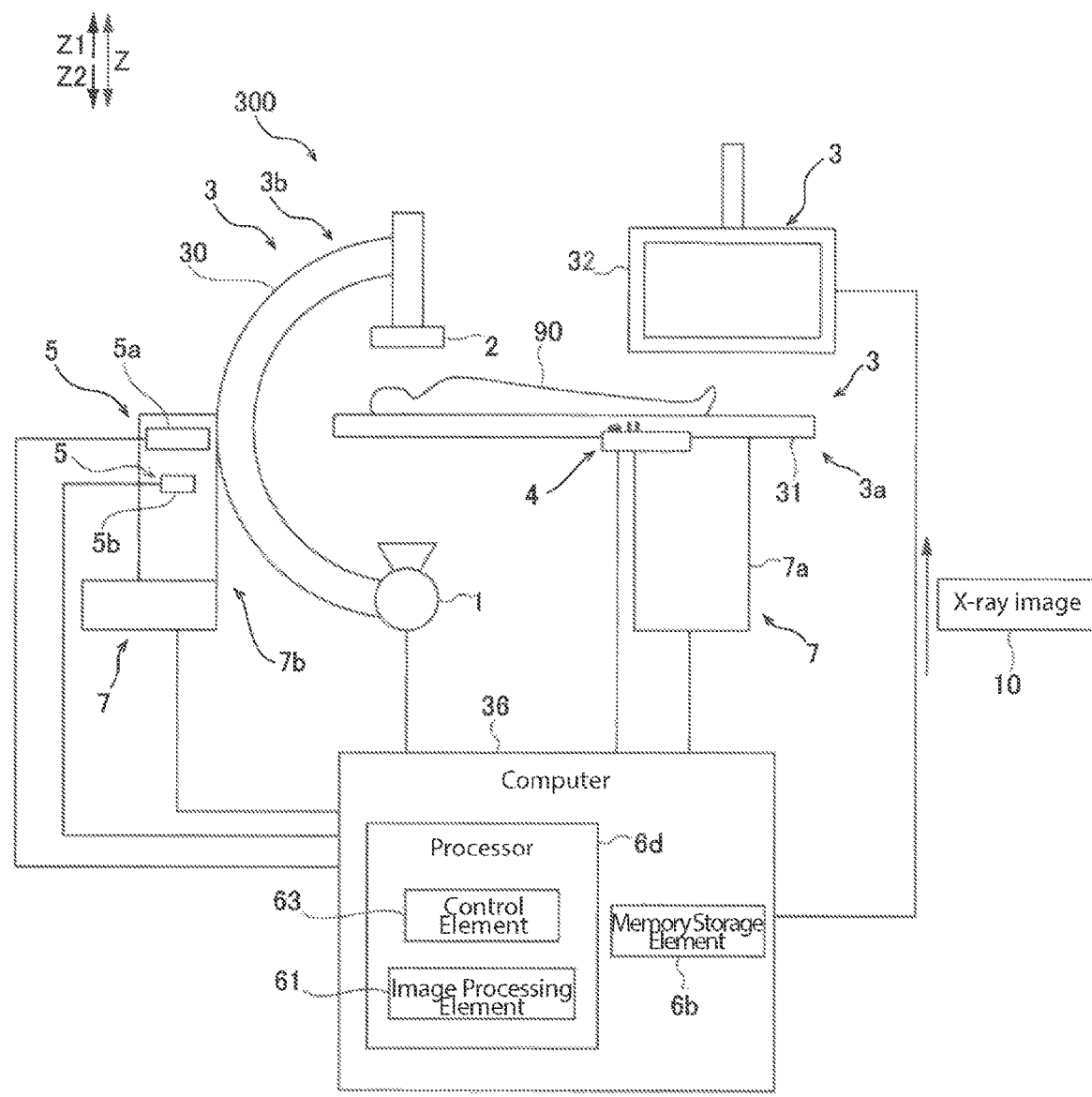
FIG. 11  Second Alternative Embodiment

X-RAY FLUOROSCOPIC IMAGING APPARATUS

CROSS REFERENCE TO RELATED APPLICATIONS

This application relates to, and claims priority from JP 2020-197561 filed November 27, the entire contents of which are incorporated herein by reference.

FIGURE SELECTED FOR PUBLICATION

FIG. 1.

BACKGROUND OF THE INVENTION

Field of the Invention

The present invention relates to an X-ray fluoroscopic imaging apparatus, and more particularly, relates to an X-ray fluoroscopic imaging apparatus that moves a plurality of imaging equipment components.

Description of the Related Art

Conventionally, an X-ray fluoroscopic imaging apparatus capable of moving a plurality of imaging equipment component members are known. Such an X-ray fluoroscopic imaging apparatus is disclosed in Patent Document JP2020-081410 A.

The X-ray imaging apparatus disclosed in JP2020-081410 A comprises a medical table, a table moving mechanism, an arm, an arm moving mechanism, a control element and an operation element. The medical table equips with a table on which a subject is loaded. In addition, the table moving mechanism moves the table. Further, the arm is maintained so as to face the x-ray irradiation element and the X-ray detection element. Further, the arm mechanism performs the turning movement around the perpendicular axis, the rotation moves around the horizontal axis, the sliding move along the arc, and the horizontal move along the horizontal direction. Further, the control element makes the arm perform at least one move selected from a group consisting of the turning move, the rotation moves, the sliding move and the horizontal move while interlocked with the horizontal shift move of the table by the table moving mechanism. Further, the operation element receives the operation input from an operator.

The X-ray imaging apparatus disclosed in JP 2020081410 A can switch back and forth the interlocking mode in which the arm moves while interlocked with the table moving movement and the non-interlocking mode in which the arm move while not interlocked with the table moving movement. The arm moves while interlocked with the moving movement of the table when the operator operates the operation element while the interlocking mode is being selected.

Herein, when the arm (C-arm) automatically moves while interlocked with the move of the table as the X-ray imaging apparatus disclosed in JP 2020081410 A and if the operator who is not fully familiar to the equipment specification operates, the C-arm may contact the operator or the technician. Specifically, when the imaging equipment component member such as the C-arm moves while interlocked with the imaging apparatus structural and given member such as the table and the operator, who is not fully familiar to the equipment specification, operates the imaging equipment component member, the imaging equipment component member, which the operator does not operate, moves as well while interlocked therewith and the imaging equipment component member that moved while interlocked therewith may contact the operator or the technician. Further, even if the operator understands the specification instructing that a plurality of the imaging equipment component members moves in interlocking, a member that the operator is not intending may move when the equipment decides which member moves while interlocked therewith. Accordingly, an X-ray fluoroscopic imaging apparatus capable of understanding which member of the imaging equipment component members moving while interlocked with the given member of the imaging equipment component members moves is desirable.

ASPECTS AND SUMMARY OF THE INVENTION

The present invention has been proposed in order to solve the aforementioned problems, and an object of the present invention is to provide an X-ray fluoroscopic imaging apparatus that allows an operator or a technician to understand which member of the imaging equipment component members moves while interlocked with the given member of the imaging equipment component members regardless the understanding level as for the equipment specification.

To achieve the above problem, according to one aspect of the present invention, an X-ray fluoroscopy imaging apparatus, comprises: a plurality of imaging equipment component members that further includes an X-ray source that irradiates an X-ray to a subject, an X-ray detector that detects the X-ray irradiated from the X-ray source, a C-arm that holds the X-ray source and the X-ray detector under conditions facing each other, a table on which a subject is loaded, and a display unit that displays an X-ray image of the subject; an input receiving element that receives an operation input by an operator; an information element that informs a move of any member of a plurality of the imaging equipment component members; and a control element, wherein the control element performs a control in which the information element informs that a second imaging equipment component member moves when performing one control of the move of a first imaging equipment component member based on a first operation input to move the first imaging equipment component member among the plurality of imaging equipment component members and another control of the move of the second imaging equipment component member different from the first imaging equipment component member of the plurality of the imaging equipment component members while interlocked with the move of the first imaging equipment component member.

The X-ray fluoroscopic imaging apparatus according to the above aspect of the present invention, the control element performs a control as for informing with the information element, in which the second imaging equipment component member moves when performing the control of the move of the second imaging equipment component member while interlocked with the move of the first imaging equipment component Accordingly, when the second imaging equipment component member moves while interlocked with the move of the first imaging equipment component member, the operator can understand the move of the second imaging equipment component member even when the operator does not understand in advance with respect to that the second imaging equipment component member moves while interlocked with the move of the first imaging equipment component member. Further, even when the X-ray fluoroscopic imaging apparatus decides the second imaging equipment component member that moves while interlocked with the first imaging equipment component member among a plurality of imaging equipment component members, the information element is capable of informing that which imaging equipment component member is the second imaging equipment component member among a plurality of the imaging equipment component members, so that the operator who is aware of that the a plurality of the imaging equipment component members moves while interlocked with one another can understand further. As results, the present invention can provide an X-ray fluoroscopic imaging apparatus that allows an operator or a technician to understand which member of the imaging equipment component members moving while interlocked with the given member of the imaging equipment component members regardless the understanding level as for the equipment specification.

The above and other aspects, features and advantages of the present invention will become apparent from the following description read in conjunction with the accompanying drawings, in which like reference numerals designate the same elements.

BRIEF DESCRIPTION OF THE DRAWINGS

FIG. 5 is a schematic view illustrating the input receiving element.

FIG. 6 is a schematic view illustrating the structure of a table operation unit, a C-arm operation unit and an X-ray detector operation element.

FIG. 7A is a schematic view illustrating a start of the table moving when the C-arm is moved while interlocked with the move of the table according to the aspect of Embodiment.

FIG. 7B is a schematic view illustrating a turning of the C-arm when the C-arm is moved while interlocked with the move of the table according to the aspect of Embodiment.

FIG. 7C is a schematic view illustrating moving the table to the position of the lower leg to be imaged when the C-arm is moved while interlocked with the move of the table according to the aspect of Embodiment.

FIG. 8 is a flow chart illustrating a processing of informing that informs the second imaging equipment component member.

FIG. 9 is a schematic view illustrating the structure of the X-ray fluoroscopic imaging apparatus according to the alternative Embodiment 1.

FIG. 11 is a schematic view illustrating the structure of the X-ray fluoroscopic imaging apparatus according to the alternative Embodiment 2.

DETAILED DESCRIPTION OF THE PREFERRED EMBODIMENTS

Figure 1:
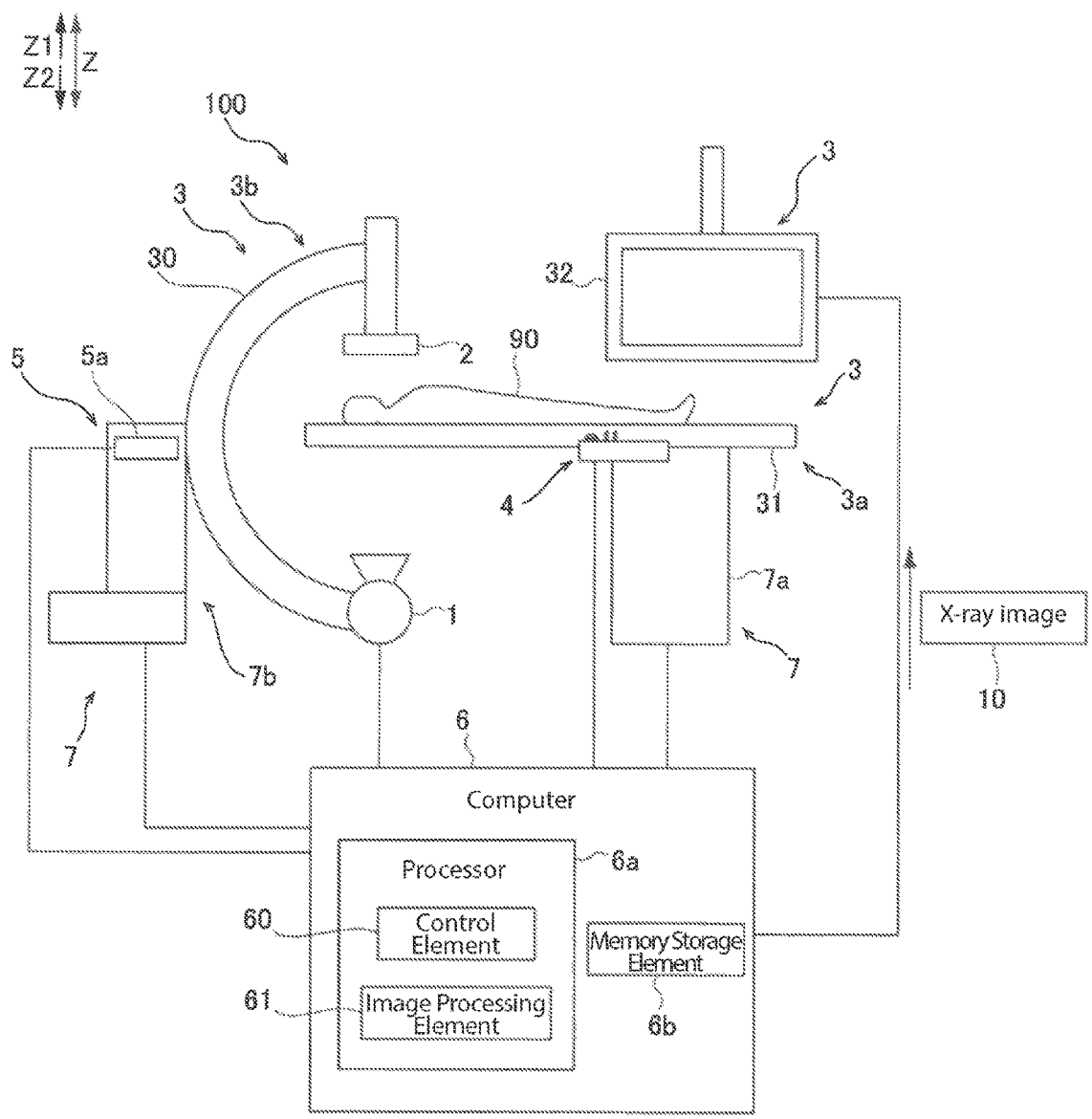
FIG. 1 is a schematic view illustrating the X-ray fluoroscopic imaging apparatus according to one aspect of Embodiment of the present invention.

Reference will now be made in detail to embodiments of the invention. Wherever possible, same or similar reference numerals are used in the drawings and the description to refer to the same or like parts or steps. The drawings are in simplified form and are not to precise scale. The word 'couple', 'link', 'connect', and similar terms do not necessarily denote direct and immediate connections, but also include connections through intermediate elements or devices. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent.

[Entire Structure of the X-Ray Fluoroscopic Imaging Apparatus]

Referring to FIG. 1-FIG. 7, the inventor illustrates the X-ray fluoroscopic imaging apparatus 100 according to an aspect of the Embodiment of the present invention.

Referring to FIG. 1, the X-ray fluoroscopy imaging apparatus 100 is an apparatus to image the blood vessel of a subject 90. The blood vessel of the subject 90 includes e.g., such as the blood vessel of the head (brain), the blood vessel of the heart (coronary artery), the blood vessel of the abdomen and the blood vessel of the lower leg.

The X-ray fluoroscopic imaging apparatus 100 according to the aspect of the Embodiment comprises an X-ray source 1, an X-ray detector 2, a plurality of the imaging equipment component members 3, an input receiving element 4, an information element 5 and a computer 6. Further, the X-ray fluoroscopy imaging apparatus 100 according to one aspect of the Embodiment comprises a plurality of moving mechanisms 7 to move the plurality of the imaging equipment component members 3.

The X-ray source 1 irradiates an X-ray toward the subject 90. The X-ray source 1 includes an X-ray tube, not shown in FIG. The X-ray tube is heated up by turning on electricity respectively to the anode and the cathode inside thereof, and when a thermal electron emitted from the cathode collides with the anode by adding a voltage, an X-ray radiates. Further, the X-ray emitted in the X-ray tube is irradiated toward the X-ray detector 2.

The X-ray detection detector 2 detects the X-ray that is irradiated from the X-ray tube 1. The X-ray detection detector 2 is e.g., a FPD (Flat Panel Detector). The X-ray detection detector 2 detects the X-ray that is irradiated by the X-ray tube 1 and then transmits the subject 90. The X-ray detector 2 has a photographic element (not shown in FIG.) having a plurality of pixels (segments) inside thereof, detects a strength of the X-ray every corresponding pixel and converts an information (detection signal) of the X-ray every pixel to an electric signal (digital data) as a pixel value. The X-ray information converted to the electric signal is sent to the control element 60.

In addition, the imaging equipment component member 3 according to an Embodiment of the present invention is the member that can be moved by the moving mechanism on imaging. The plurality of imaging equipment component members 3 includes the C-arm 30, the table 31 and the display unit 32.

The C-arm 30 has an arc like shape. The C-arm 30 holds the X-ray source 1 and the X-ray detector 2 to be facing each other. Specifically, the X-ray source 1 connects to one end of the C-arm 30, and the X-ray detector 2 connects to another end thereof. The C-arm 30 allows the X-ray source 1 and the X-ray detector 2 to be in place facing each other while sandwiching the subject 90 lying on the table 31. The X-ray fluoroscopy imaging apparatus 100 according to the present Embodiment has a single-plane type with one C-arm 30.

The C-arm 30 is installed to the C-arm moving mechanism 7b, set forth later, as being movable. The C-arm 30 is configured to be movable in turning and moving in parallel by the C-arm moving mechanism 7b.

The subject 90 is loaded on the table 31. The subject 90 is loaded on the table 31 so that the long direction of the table 31 and the direction between the head and the foot of the subject 90 are the same direction. Here, referring to FIG. 1, the long direction of the table 31 denotes an X-direction. Further, the direction toward to the heard of the subject 90 denotes X1-direction, and the direction toward the foot denotes X2-direction. Further, the short direction (direction from right to left direction of the subject 90) of the table 31 orthogonal to the X-direction denotes the Y-direction. Further, When the subject is lying on the back thereof, the direction toward the right hand of the subject 90 denotes Y1-direction, and the direction toward the left hand of the subject denotes Y2-direction. Further, the orthogonal direction to both X-direction and Y-direction denotes the Z-direction. Further, the direction upward denotes Z1-direction, and the direction downward denotes Z2-direction. The table moving mechanism 7a allows the table 31 to move in the X-direction, Y-direction and Z-direction while the subject is being loaded.

The display unit 32 displays an X-ray image 10 of the subject 90. The display unit 32 includes such as a liquid crystal display monitor.

The input receiving element 4 receives the operation input from the user. The input receiving element 4 is installed to the table 31. The inventors set forth the detail of the input receiving element 4 later.

The information element 5 informs to the operator or the technical personnel which one member of a plurality of the imaging equipment component members 3 moves. According to an Embodiment, the information element 5 includes the light emission element 5a that informs by emitting the light. The light emission element 5a includes e.g., such as LED (Light Emitting Diode). Further, referring to FIG. 1, the light emission element 5a is a linear light source extending along the X-direction.

According to the present Embodiment, the information element 5 is at least one of the second imaging equipment component member 3b and the moving mechanism 7 that is one of the pluralities of the moving mechanisms 7 and moves the second imaging equipment component member 3b. According to the present Embodiment, the information element 5 is installed to one side and the other side of the moving mechanism 7 that is one of the pluralities of the moving mechanisms 7 and moves the second imaging equipment component member 3b. Specifically, the information element 5 is installed to the C-arm moving mechanism 7b. According to the present Embodiment, the information element 5 is installed to the Y1-direction side plane of the C-arm moving mechanism 7b and the Y2-direction side plane thereof.

The computer 6 includes a processor 6a and a memory storage element 6b.

The processor 6a includes the control element 60 and the image processing element 61. The processor 6a includes e.g., such as CPU (Central Processing Unit), GPU (Graphics Processing Unit) and FPGA (Field-Programmable Gate Array) for imaging processing. The control element 60 is configured software-wise to be a functional block brought into reality by that the processor 6a executes a variety of programs. The control element 60 can be configured hardware-wise by installing the exclusive processor (process circuit).

According to the present Embodiment, the control element 60, wherein the control element performs a control in which the information element 5 informs that a second imaging equipment component member 3b moves when performing one control of the move of the first imaging equipment component member 3a based on a first operation input to move the first imaging equipment component member 3a among the plurality of imaging equipment component members 3 and another control of the move of the second imaging equipment component member 3b different from the first imaging equipment component member 3a of the plurality of the imaging equipment component members 3 while interlocked with the move of the first imaging equipment component member 3a. In addition, the first imaging equipment component member 3a is a member moved by that the operator operates intentionally. Further, the second imaging equipment component member 3b is another member moved while interlocked with the first imaging equipment component member 3a due to the control that the control element 60 provides. The inventors illustrate an example according to the present Embodiment, wherein the first imaging equipment component member 3a is the table 31 and the second imaging equipment component member 3b is the C-arm 30. Further, the move in which the second imaging equipment component member 3b moves while interlocked with the first imaging equipment component member 3a means that the second imaging equipment component member 3b moves due to the operation that allows the first imaging equipment component member 3a to move. Specifically, the move in which the second imaging equipment component member 3b moves while interlocked with the first imaging equipment component member 3a means that the second imaging equipment component member 3b also moves while the first imaging equipment component member 3a is moving.

The memory element 6b stores such as a variety of programs which the processor 6a executes and an X-ray image 10 which the image processing element 61 generates. The memory storage element 6b includes a non-volatile memory such as e.g., an HDD (Hard Disk Drive) and an SSD (Solid State Drive).

A plurality of moving mechanism 7 moves at least two of a plurality of the imaging equipment component members 3. According to the present Embodiment, the plurality of the moving mechanism 7 has the table moving mechanism 7a which moves the table 31 and the C-arm moving mechanism 7b which moves the C-arm 30.

The table move mechanism 7a enables the table 31 to be moved in the X-direction, Y-direction and Z-direction. The table move mechanism 7a includes a linear move mechanism in the X-direction, a linear move mechanism in the Y-direction and the linear move mechanism in the Z-direction.

The C-arm moving mechanism 7b is configured to allow the C-arm 30 to turn and shift in parallel. The inventors set forth the detail structure of the C-arm moving mechanism 7b.

(C-Arm Angle)

Figure 2A:
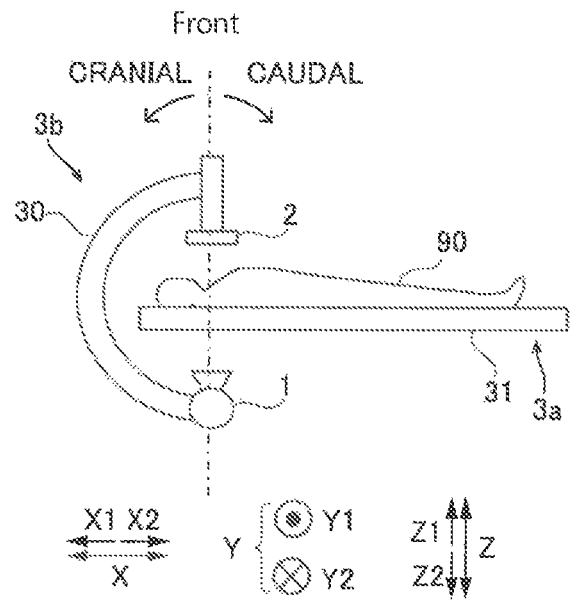
FIG. 2A is a schematic view illustrating the imaging direction from the side of the subject.
Figure 2B:
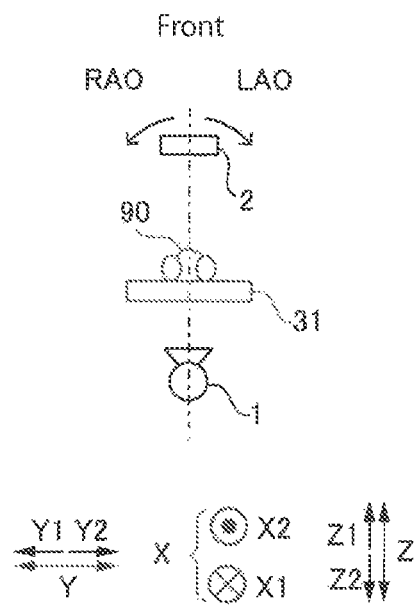
FIG. 2B is a schematic view illustrating the imaging direction from the foot side of the subject.

The X-ray fluoroscopy imaging apparatus 100 is capable of imaging the subject 90 in the direction, in which the X-ray is irradiated obliquely relative to the subject 90 from one end (cranial) or the other end (caudal) in the longitudinal plane along the long direction (X-direction) of the table 31 on which the subject 90 is loaded referring to FIG. 2A, from an arbitrary combination direction of the respective directions of the right anterior oblique (RAO) direction, the front direction and the left anterior oblique (LAO) direction referring to FIG. 2B. In addition, referring to FIG. 2B, the C-arm 30 is not shown.

(Imaging Position)

Figure 3:
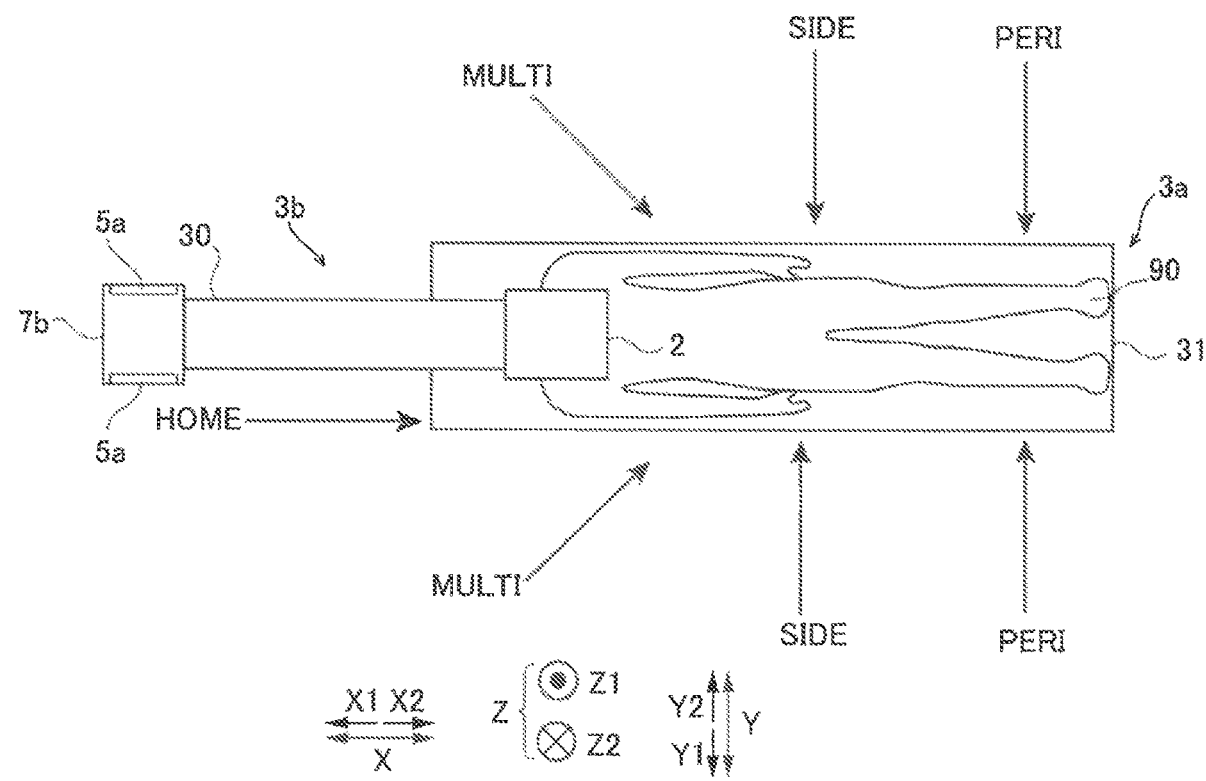
FIG. 3 is a schematic view illustrating the relative location between the table and the X-ray detector.

Referring to FIG. 3, the relative position (imaging position) of the C-arm to the table 31 varies depending on an imaging region. Referring to FIG. 3, the respective arrow directions are the directions in which the C-arm 30 is inserted relative to the table 31, wherein the X-ray detector 2 positions at the tip side of the arrow, i.e., subject 90 side, and the C-arm moving mechanism 7b positions at the rear end (opposite end of the tip) side of the arrow. The position in which the C-arm 30 is in place along the long side of the table 31 (X-direction) is defined as HOME position. Further, the position in which the C-arm 30 is in place obliquely as the direction thereof is toward the foot side (X2-direction) of the subject from the head side (X1-direction) of the subject 90 and is toward the subject 90 from the long direction (X-direction) of the table 31 is defined as MULTI position. Specifically, the MULTI position is the position at which the C-arm 30 is in place obliquely at the head side of the subject 90 from the center position of the table 31.

Further, the position in which the C-arm 30 is in place along the short side of the table 31 (Y-direction) toward the center from the side of the subject 90 at the top view is defined as SIDE position. Specifically, the SIDE position is the position at which the C-arm 30 is in place laterally (direction along the Y-direction) near the center of the table 31 in the long direction (X-direction) of the table 31. In addition, the position moved toward the foot side of the subject 90 from the SIDE position is defined as the PERI position. Specifically, the PERI position is the position at which the C-arm 30 is in place laterally at the foot side of the subject 90 from the center position of the table 31 in the long direction of the table 31 (X-direction). For example, when the imaging from the head to the chest of the subject 90 is conducted, the HOME position is applied thereto. Further, when the imaging of the lower leg is conducted, the PERI position is applied thereto. Further, when the imaging of the abdomen of the subject 90 is conducted, the MULTI or SIDE position is applied thereto. In addition, the respective positions of the HOME position, the MULTI position, the SIDE position and the PERI position define the facing direction of the C-arm 30 and the relative position between the C-arm 30 and the table 31 (the respective position coordinates of the C-arm 30 and the table 31).

(C-Arm Moving Mechanism)

Figure 4:
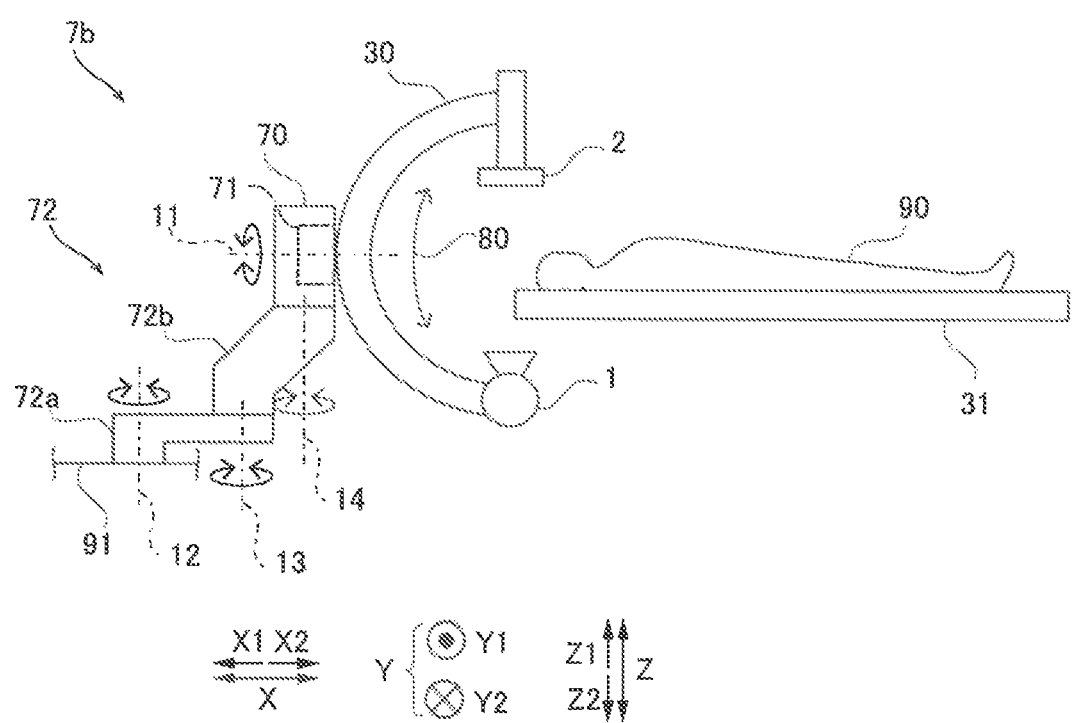
FIG. 4 is a schematic view illustrating the structure of the C-arm moving mechanism according to the aspect of the Embodiment 1 of the present invention.

Referring to FIG. 4, the C-arm moving mechanism 7b includes an arm pedestal 70, a rotation mechanism 71 and the moving mechanism 72. Referring to FIG. 4, the rotation mechanism 71 rotates the C-arm 30 around the shaft line of a rotation shaft 11 extending in the long side (X-direction) of the table 31 which is the line connecting the head and the feet of the subject 90. Further, the rotation mechanism 71 allows the C-arm 30 to rotate in the circumferential direction 80 of the C-arm 30, wherein the line extending in the short direction, which is the right-to-left direction of the subject 90, (Y-direction) of the table 31 is the shaft thereof. Such as the rotation mechanism 71 includes e.g., a motor and so forth.

The moving mechanism 72 is installed to the arm pedestal 70. The C-arm 30 can be horizontally moved in accordance with the horizontal move of the arm pedestal 70 moved by the moving mechanism 72. The moving mechanism 72 includes a first rotation element 72a installed on the floor surface 91 and the second rotation element 72 which is held rotatably by the first rotation element 72a and holds the arm pedestal 70 rotatably. The rotation element 72a includes the pedestal 12 and a mid-shaft 13 in place at the distant position from the pedestal 12. The second rotation element 72 includes a horizontal rotation shaft 14.

The pedestal shaft 12 and the mid-shaft 13 are respectively rotation shafts in the perpendicular direction to the floor surface 91. Further, the horizontal rotation shaft 14 is also a rotation shaft in the perpendicular direction to the floor surface 91. Accordingly, the moving mechanism 72 can move horizontally the arm pedestal 70 and the C-arm 30 to the desired position by combining the rotation around the shaft line of the pedestal shaft 12, the rotation around the shaft line of the mid-shaft 13 and the rotation around the shaft line of the horizontal rotation shaft 14.

(Input Receiving Element)

Referring to FIG. 5, an input receiving element 4a includes the table operation element, the C-ram operation element 4b, the X-ray detector operation element 4c and a move mode selection element 4d.

The table operation element 4a moves the table 31 while the operator is pressing down the table operation element 4a under the state in which the move mode selection element 4d selects the predetermined move mode. Specifically, the table operation element 4a moves the table 31 to the move target place while the operator is pressing down the table operation element 4a under the state in which the move target place (position) for the table 31 is predetermined in advance. The operation element 4a includes e.g., a press button.

The C-arm operation element 4b moves the C-arm 30 while the operator operates the C-arm operation element 4b. The C-arm operation element 4b includes e.g., a lever switch. The inventors set forth the detail of the C-arm operation element 4b.

The X-ray detector operation element 4c moves the X-ray detector 2 back and forth in the X-ray irradiation axis direction while the operator operates the X-ray detector operation element 4c. The X-ray detection operation element 4c includes e.g., a lever switch. The inventors set forth the detail of the X-ray detector operation element 4c later.

The move mode selection element 4d can receive the input of move mode of the imaging equipment component member 3. The move mode selection element 4d includes e.g., a press button. The move mode of the imaging equipment component member 3 includes such as a femoral approach mode in which the lower leg is imaged, a memory mode in which the C-arm 30 and the table 31 moves to the preset position and a free mode in which the C-arm 30 and the table 31 moves to an arbitrary position. The operator presses down the move mode selection element 4d for the desired move mode and moves the imaging equipment component member 3 using the desired move mode while operating at least any one element selected from a group consisting of the table operation element 4a, the C-arm operation element 4b and the X-ray detector operation element 4c.

Referring to FIG. 6, the C-arm operation element 4b includes a first lever element 40, a rotation selection button 41 and a horizontal move selection button 42. The operator tilts the first lever element 40 while the operator is pressing down the rotation selection button 41, so that the operator can tilt the C-arm 30 to the desired angle given by combining CRANIAL or CAUDIAL and RAO or LAO. Further, the operator tilts the first lever element 40 while the operator is pressing down a horizontal moving selection button 42, so that the operator can move the C-arm horizontally.

Further, referring to FIG. 6, the X-ray detector operation element 4c includes a second lever element 43, an X-ray detector move button 44. The operator tilts the second lever element 43 while the operator is pressing down X-ray detector move button 44, so that the operator can move the X-ray detector 2 back and forth in the X-ray irradiation axis direction.

(Move of the Table and the C-Arm)

Next, referring to FIG. 7A to FIG. 7C, the inventors set forth the move of the C-arm 30 while interlocked with the move of the table 31. The Embodiment illustrated in FIG. 7A to FIG. 7C illustrates the move of the C-arm 30 and the table 31 when the femoral approach mode is selected using the move mode selection element 4d (referring to FIG. 5).

Referring to FIG. 7A, the control element 60 moves the table 31 in the direction indicated by the arrow sign 81 to image the lower leg of the subject 90 when the femoral approach mode is selected under the condition in which the C-arm 30 is inserted from the head side (X1-direction side) of the subject 90.

At this time, referring to FIG. 7A, the C-arm 30 is in place in the move direction (X-direction) side of the table 31, so that the table 31 cannot be moved under such a condition as-is. If the operator moves the C-arm 30, the table 31 can be moved in the direction indicated by the arrow sign 81, but the number of the operations by the operator increase, and the burden therefor increases. Then according to the femoral approach mode, when the operation conducts to move the table 31, the C-arm 30 moves white interlocked with the move of the table 31. Specifically, referring to FIG. 7B, the C-arm 30 turns in the direction indicated by the arrow sign 82 while interlocked with the move of the table 31. Referring to FIG. 7C, the control element 60 controls the move of the table 31 in the direction indicated by the arrow sign 81 while turning the C-arm 30 until of which position does not interfere the table 31 so that the table 31 moves to the position at which the lower leg of the subject 90 is imaged. In addition, according to the present Embodiment, the control element 60 controls the table moving mechanism 7a and the C-arm moving mechanism 7b so that the table 31 and the C-arm 30 moves simultaneously and in parallel.

Here, given the operator does not comprehend that the C-arm 30 moves while interlocked with the move of the table 31 in the femoral approach mode, the C-arm 30 may contact such as operator and technical personnel.

(Information Processing by Control Element)

Then, according to the present Embodiment, the control element 60 controls the information element 5 to inform in advance prior to starting the move of the first imaging equipment component member 3a (table 31) based on the first operation input when receiving an input of the move mode (femoral approach mode) for moving the second imaging equipment component member 3b (C-arm 30) while interlocked with the move of the first imaging equipment component member 3a (table 31) as the second operation input. Specifically, according to the present Embodiment, the control element 60 controls the information element 5 (light emission element 5a) to inform prior to starting the move of the table 31 as the first imaging equipment component member 3a when receiving an operation input for moving the table 31 as the first operation input. Specifically, according to the present Embodiment, the control element 60 controls the information element 5 for informing that the C-arm 30 moves when performing the control of the move of the C-arm 30 as the second imaging equipment component member 3b by the C-arm moving mechanism 7b while interlocked with the move of the table 31 as the first imaging equipment 3a by the table moving mechanism 7a.

Further, according to the present Embodiment, the control element 60 decides whether the second imaging equipment component member 3b should be moved or not while interlocked with the move of the first imaging equipment component member 3a (table 31) without receiving the operation input from the operator for moving the second imaging equipment component member 3b (C-arm 30). Specifically, the control element 60 decides whether the second imaging equipment component member 3b (C-arm 30) should be moved while interlocked with the move of the first imaging equipment component member 3a (table 31) when receiving the second operation input. Here, in the case of that the control element 60 decides whether the second imaging equipment component member 3b should be moved or not, even if the operator understands the specification in which a plurality of the imaging equipment component members 3 moves respectively while interlocked with one another, the operator cannot be aware of which imaging equipment component member 3 moves while interlocked with one another. Then, according to the present Embodiment, the control element 60 conducts informing using the information element 5 when the second imaging equipment component member 3b is moved while interlocked with the move of the first imaging equipment component member 3a (table 31) and does not conduct informing using the information element 5 when the second imaging equipment component member 3b (C-arm 30) should not be moved while interlocked with the move of the first imaging equipment component member 3a.

Specifically, when the first imaging equipment component member 3a (table 31) is moved to the predetermined position based on the first operation input, the control element 60 acquires the present position 50 that is the position before the second imaging equipment component member 3b (C-arm 30) moves and the target position 51 that is the position after the second imaging equipment component member 3b (C-arm 30) moves, and also performs the control in which when the present position and the target position are different, the information element 5 informs, and when the present position 50 and the target position 51 are the same, the information element 5 does not inform. In addition, the control element 60 acquires the present position 50 from the potentiometer installed to a driving element (not shown in FIG.) of the C-arm moving mechanism 7b. Further, the control element 60 acquires the target position 51 from the memory storage element 6b based on the selected move mode.

(Information Method Using Information Element)

According to the present Embodiment, the control element 60 controls to provide the information as to the move of the second imaging equipment component member 3b (C-arm 30) by controlling the light emission from the light emission element 5a (information element 5). According to the present Embodiment, the control element 60 controls to provide the information as to the move of the second imaging equipment component member 3b by differentiating the light emission aspect of the light emission element 5a. Specifically, the control element 60 controls as the light emission element 5a is lighting on while the X-ray fluoroscopic imaging apparatus 100 is working, and when the C-arm 30 moves while interlocked with the move of the table 31, the control for informing is conducted to change the light emission element 5a from the lighting-on state to the light flashing state.

(Information Processing)

Next, referring to FIG. 8, the inventors set illustrates an information processing in which the control element 60, according to the present Embodiment, initiates the information element 5 to inform that the second imaging equipment component member 3b (C-arm 30) moves, At Step 101, the control element 60 decides whether there is the second operation input or not relative to the mode (femoral approach mode) in which the second imaging equipment component member 3b (C-arm 30) moves while interlocked with the first imaging equipment component member 3a (table 31). When there is the second operation input, the processing proceeds to Step 102. When there is no second operation input, the control element 60 repeats the processing of Step 101.

At Step 102, the control element 60 acquires the present position 50 of the C-arm 30. In the processing of Step 102, the control element 60 acquires the angle of the C-arm 30 and the position coordinate as the present position 50 of the C-arm 30 from the C-arm moving mechanism 7b.

At Step 103, the control element 60 acquires the target purpose position 51 of the C-arm 30. In the processing of Step 103, the control element 60 acquires the angle of the C-arm 30 and the position coordinate as the target position 51 of the C-arm 30 from the memory storage element 6b.

At Step 104, the control element 60 decides whether the present position 50 and the target position 51 are the same or not. When the present position 50 and the target position 51 are the same, the processing proceeds to Step 106. Specifically, when the present position 50 and the target position 51 are the same, the C-arm 30 does not move, so that the control element 60 does not conduct the information element 5 to inform any. When the present position 50 and the target position 51 are not the same, the processing proceeds to Step 105.

At Step 105, the control element 60 conducts to provide the information by the information element 5. Specifically, the control element 60 conduct to provide the information by emitting the light from the information element 5 (light emission element 5a). Specifically, the control element 60 conducts to provide the information by changing the lighting aspect from the lighting-on state to the light flashing state of the light emission element 5a.

At the step 106, the control element 60 decides whether there is the first operation input or not. When there is the first operation input, the processing proceeds to Step 107. When there is no operation input, the control element 60 repeats the processing of Step 106.

At Step 107, the control element 60 moves the first imaging equipment component member 3a (table 31) and the second imaging equipment component member 3b (C-arm 30) by controlling the table moving mechanism 7a and the C-arm moving mechanism 7b.

At Step 108, Specifically, the control element 60 decides whether the second imaging equipment component member 3b (C-arm 30) moves to the predetermined position or not. When the table 31 and the C-arm 30 moves to the predetermined position, the processing proceeds to Step 109, When the table 31 and the C-arm 30 have not moved to the predetermined position, the processing proceeds to Step 107, At Step 109, the control element 60 suspends the information element 5 (light emission element 5a) to provide the information. Then after, the processing ends. In addition, when the present position 50 and the target position 51 are the same, the processing at Step 109 is skipped.

In addition, any one of the processing at Step 102 or the processing at Step 103 may be conducted first.

According to the present Embodiment, practically, the information processing by the control element 60 and the input of the second operation, in which the move mode is selected, are conducted simultaneously. In other words, the control element 60 starts to provide the information in-between from receiving the selection of the move mode to starting the action (receiving the first operation input).

Effect of the Present Embodiment

The following effect can be obtained according to the present Embodiment.

According to the present Embodiment 1, as set forth above, the X-ray fluoroscopic imaging apparatus 100 comprises: a plurality of imaging equipment component members further comprising: an X-ray source 1 that irradiates an X-ray to a subject 90; an X-ray detector 2 that detects the X-ray irradiated from the X-ray source 1; a C-arm 30 that holds the X-ray source 1 and the X-ray detector 2 under the condition facing each other; a table 31 on which the subject 90 is loaded; a display unit 32 that displays an X-ray image 10 of the subject 90; an input receiving element 4 that receives an operation input by an operator an information element 5 that informs a move of any member of the plurality of the imaging equipment component members 3; and a control element 60, wherein the control element 60 performs a control in which the information element 5 informs that a second imaging equipment component member 3b moves when performing one control of the move of a first imaging equipment component member 3a based on a first operation input to move the first imaging equipment component member 3a (table 31) among the plurality of imaging equipment component members 3 and another control of the move of the second imaging equipment component member 3b (C-arm 30) different from the first imaging equipment component member 3a of the plurality of the imaging equipment component members 3 while interlocked with the move of the first imaging equipment component member 3a.

Accordingly, when the second imaging equipment component member 3b (C-arm 30) moves while interlocked with the move of the first imaging equipment component member 3a (table 31), the information element 5 informs that the second imaging equipment component member 3b moves, so that the operator can understand that the second imaging equipment component member 3b moves even when the operator does not understand in advance with respect to that the second imaging equipment component member 3b moves while interlocked with the move of the first imaging equipment component member 3a. Further, even when the X-ray fluoroscopic imaging apparatus 100 identifies the second imaging equipment component 3b member that moves while interlocked with the first imaging equipment component member 3a among the plurality of imaging equipment component members 3, the information element 5 can inform that which imaging equipment component member is the second imaging equipment component member 3b among the plurality of the imaging equipment component members 3, so that the operator who is aware of that a plurality of the imaging equipment component members 3 moves while interlocked with one another can understand which imaging equipment component member 3 moves. As a result, the present invention can provide an X-ray fluoroscopic imaging apparatus 100 that allows an operator or a technician to understand which member of the imaging equipment component members 3 moving while interlocked with the given member of the imaging equipment component members 3 regardless the understanding level as for the equipment specification.

Further, with regard to the present Embodiment, the more effect below can be obtained due to the following structure.

Specifically, according to the present Embodiment and as set forth above, the control element 60 controls the information element 5 to inform in advance prior to starting the move of the first imaging equipment component member 3a based on the first operation input when receiving an input of the move mode for moving the second imaging equipment component member 3b (C-arm 30) while interlocked with the move of the first imaging equipment component member 3a (table 31) as the second operation input. Accordingly, when received the second operation input, the move of the second imaging equipment component member 3b is informed, so that the move of the second imaging equipment component member 3b can be informed before the second imaging equipment component member 3b starts moving. As a result, the operator can assuredly understand that the second imaging equipment component member 3b moves before the second imaging equipment component member 3b starts moving.

Further, according to the present Embodiment, as set forth above, the control element 60 decides whether the second imaging equipment component member 3b (C-arm 30) should be moved or not while interlocked with the move of the first imaging equipment component member 3a (table 31) when received the second operation input, and also when the second imaging equipment component member 3b moves while interlocked with the first imaging equipment component member 3a, the information element 5 informs and whereas, when the second imaging equipment component member 3b is not moved while interlocked with the first imaging equipment component member 3a, the information element 5 does not inform. Here, when the information element 5 informs without deciding whether the second imaging equipment component member 3b moves or not while interlocked with the first imaging equipment component member 3a, the information element 5 informs even when the second imaging equipment component member 3b does not move while interlocked with the first imaging equipment component member 3a. Therefore, the operator may not accurately understand whether the second imaging equipment component member 3b moves or does not. As set forth above, the informing is conducted when the second imaging equipment component member 3b moves and not conducted when the second imaging equipment component member 3b is not moved, so that the move of the second imaging equipment component member 3b can be informed only when the second imaging equipment component member 3b moves while interlocked with the first imaging equipment component member 3a. Therefore, when the information element 5 informs, the operator can understand without fail that the second imaging equipment component member 3b moves. As a result, it is different from the case in which the information element informs the incident even when the second imaging equipment component member 3b does not move, so that it can be avoided that the operator confuses.

Further, according to the present Embodiment, as set forth above, when the first imaging equipment component member 3a (table 31) is moved to the predetermined position based on the first operation input, the control element 60 acquires the present position 50 that is the position before the second imaging equipment component member 3b (C-arm 30) moves and the target position 51 that is the position after the second imaging equipment component member 3b moves, and also performs the control in which when the present position 50 and the target position 51 are different, the information element 5 informs, and when the present position 50 and the target position 51 are the same, the information element 5 does not inform. Accordingly, the control element 60 decides whether the present position 50 and the target position 51 are the same or not, so that it can be easily decided whether the information element 5 informs or does not.

Further, according to the present Embodiment as set forth above, the plurality of moving mechanisms 7 that move at least two members of the plurality of the imaging equipment component members 3 are further provided, and the information element 5 is installed to at least one of the second imaging equipment component member 3b (C-arm 30) and the moving mechanism 7 (C-arm moving mechanism 7b) that moves the second imaging equipment component member 3b among the plurality of the moving mechanisms 7. Accordingly, the information element 5 is installed to any one of the second imaging equipment component member 3b that moves while interlocked with the first imaging equipment component member 3a (table 31) and the moving mechanism 7 that moves the second imaging equipment component member 3b, so that the information element 5 can inform near the member that actually moves. As a result, it is different from the structure, e.g., in which a move of the second imaging equipment component member 3b is displayed on such as a monitor installed as fixed to the predetermined position, and even when the operator is in the position where the operator cannot see such as a monitor, the operator or the technician can understand that the second imaging equipment component member 3b moves.

Further, according to the present Embodiment as set forth above, the information element 5 is installed to one side and the other side of the moving mechanism 7 (C-arm moving mechanism 7b) that moves the second imaging equipment component member 3b (C-arm 30). Accordingly, the information element 5 is installed to both sides of the moving mechanism 7 that moves the second imaging equipment component member 3b, so that the information from the information element 5 can be understood by the operator and the technician even when the operator is any side of the moving mechanism 7 that moves the second imaging equipment component member 3b.

Further, according to the present Embodiment as set forth above, the table moving mechanism 7a that moves the table 31 and the C-arm moving mechanism 7b that moves the C-arm 30 are further included, and the control element 60 controls the information element 5 for informing that the C-arm 30 moves when conducting the control of the move of the C-arm 30 as the second imaging equipment component member 3b by the C-arm moving mechanism 7b while interlocked with the move of the table 31 as the first imaging equipment component 3a by the table moving mechanism 7a. Accordingly, the information element 5 informs that the C-arm 30 moves while interlocked with the move of the table 31, so that the structure according to the present Embodiment is desirable relative to the X-ray fluoroscopic imaging apparatus 100, wherein the C-arm 30 moves while interlocked with the move of the table 31.

Further, according to the present Embodiment as set forth above, the information element 5 includes the light emission element 5a that informs by emitting the light. Therefore, the operator and the technician can easily understand that the second imaging equipment component member 3b moves, visually by the light emitted from the light emission element 5a. Further, the move of the second imaging equipment component member 3b is informed by the light emitted from the light emission element 5a, which is different from the structure, e.g., in which moving of the second imaging equipment component member 3b is displayed on such as the display unit 32, so that even when the operator is not accurately understanding the information displayed on the display unit 32, the operator and the technician can intuitively understand that the second imaging equipment component member 3b moves.

A Further Alternative Embodiment of the Present Embodiment

Referring to FIG. 9, and FIG. 10, the inventors set forth a further alternative Embodiment 1. In addition, the same element as illustrated according to the Embodiment 1 has the same reference sign, but the explanation thereof is skipped.

The X-ray fluoroscopic imaging apparatus 200 according to the alternative Embodiment 1 has a computer 26 instead of the computer 6 and further a display unit moving mechanism 7c that moves the display unit 32 so such a point is different from the X-ray fluoroscopic imaging apparatus 100 according to the present Embodiment as set forth above. The computer 26 according to the alternative Embodiment 1 has a processor 6c instead of the processor 6a, so such a point is different from the computer 6 according to the Embodiment as set forth above. The processor 6c according to the alternative Embodiment 1 has a control element 62 instead of the control element 60, so such a point is different from the processor 6a according to the Embodiment as set forth above.

The display unit moving mechanism 7c moves the display unit 32 in the X-direction and the Y-direction. The display unit 7c includes e.g., the linear moving mechanism in the X-direction, the linear moving mechanism in the Y-direction. In addition, the display moving mechanism 7c may move the display unit 32 in the Z-direction.

Further, according to the Alternative Embodiment 1 referring to FIG. 9, the information element 5 (light emission element 5a) is installed to the display unit 32.

Figure 10A:
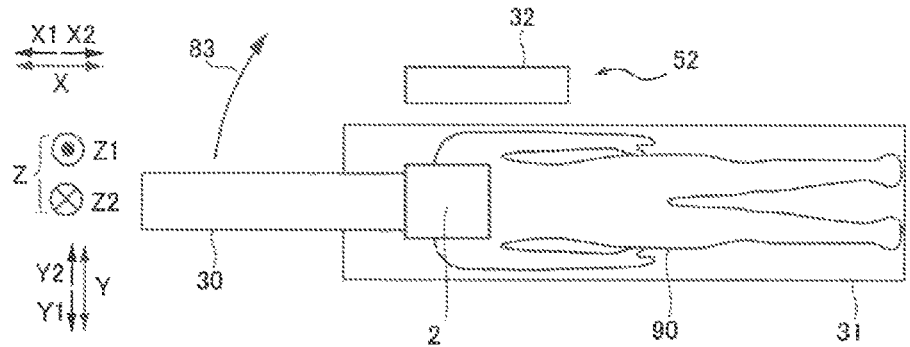
FIG. 10A is a schematic view illustrating a start of the C-arm turning when the display unit is moved while interlocked with the move of the C-arm according to the alternative Embodiment 1.
Figure 10B:
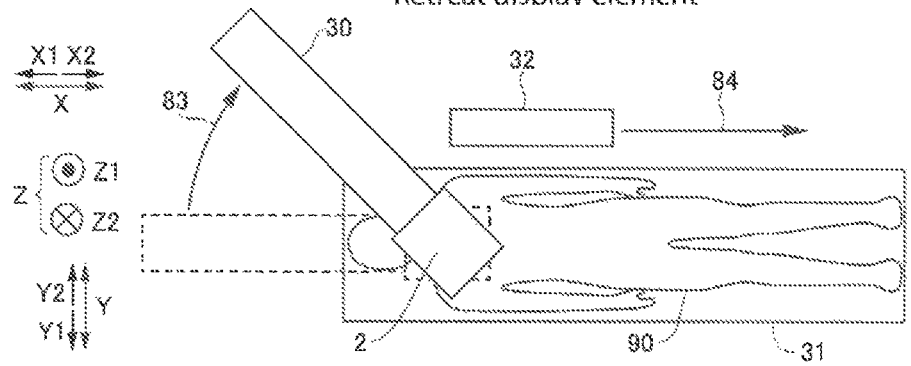
FIG. 10B is a schematic view illustrating a retreating of the display unit when the display unit is moved while interlocked with the move of the C-arm according to the alternative Embodiment 1.
Figure 10C:
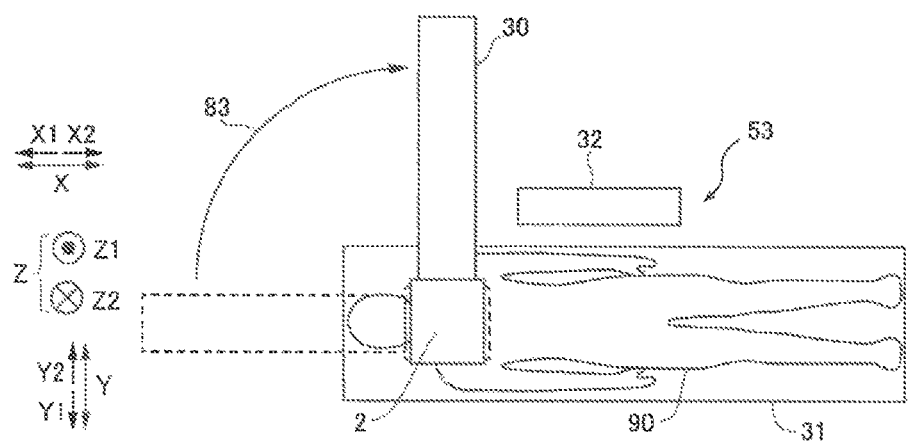
FIG. 10C is a schematic view illustrating a turning of the C-arm to the predetermined position when the C-arm is moved while interlocked with the move of the C-arm according to the alternative Embodiment 1.

Referring to FIG. 10A through FIG. 10C according to the alternative Embodiment 1, the control element 62 performs a control for moving the display unit 32 in the direction indicated by the arrow sign 84 while interlocked with the move of the C-arm 30 when turning the C-arm 30 along the arrow sign 83 and the display unit 32 is in place in the turn trajectory of the C-arm 30.

Further, according to the alternative Embodiment 1, the control element 62 controls the information element 5 (referring to FIG. 9) for informing that the display unit 32 moves when moving the display unit 32 as the second imaging equipment component member 3b by the display moving mechanism 7c while interlocked with the move of C-arm 30 by the C-arm moving mechanism 7b.

According to the alternative Embodiment 1, the control element 62 decides whether the second imaging equipment component member 3b (display unit 32) should be moved or not while interlocked with the move of the first imaging equipment component member 3a (C-arm 30) when received the operation input to move the C-arm 30. Further, the control element 62 conducts the information element 5 to inform when moving the display unit 32 while interlocked with the move of the C-arm 30 and does not conduct the information element 5 to inform when the display unit 32 does not move while interlocked with the move of the C-arm 30. Specifically, the control element 62 acquires the present position 52 that is the position before the display unit 32 moves and the target position 53 that is the position after the display unit moved and controls the information element 5 to inform when the present position and the target position are different, and whereas when the present position 52 and the target position 53 are the same, the information element 5 does not inform. In addition, the control element 62 acquires the present position 52 from the display moving mechanism 7c. Further, the control element 62 acquires the target position 53 from the memory storage element 6b.

Other structural elements according to the alternative Embodiment 1 are the same as the Embodiment as set forth above.

Effect of Alternative Embodiment 1

According to the alternative Embodiment 1 as set forth above, the X-ray fluoroscopy imaging apparatus 200 further comprises the C-arm moving mechanism 7b that moves the C-arm 30 and display unit moving mechanism 7c that moves the display unit 32, and the control element 62 controls the information element 5 for informing that the display unit 32 moves when moving the display unit 32 as the second imaging equipment component member 3b by the display moving mechanism 7c while interlocked with the move of C-arm 30 as the first imaging equipment component member 3a by the C-arm moving mechanism 7b. Accordingly, the information element 5 informs that the display unit 32 moves while interlocked with the move of the C-arm 30, so that the structure according to the alternative Embodiment 1 is desirable relative to the X-ray fluoroscopic imaging apparatus 200, wherein the display unit 32 moves while interlocked with the move of the C-arm 30.

Other effects according to the alternative Embodiment 1 is the same as the aspects of the Embodiment 1 as set forth above.

Alternative Embodiment 2 of the Present Embodiment

Referring to FIG. 11, the inventors illustrate the alternative Embodiment 2. In addition, the same element as illustrated according to the Embodiment set forth above has the same reference sign, but the explanation thereof is skipped.

Referring to FIG. 11, the X-ray fluoroscopy imaging apparatus 300 according to the alternative Embodiment 2 comprises the information element 5 having a speaker 5b that outputs the information sound and the computer 36 instead of the computer 6 and is different from the X-ray fluoroscopy imaging apparatus 100 according to the present Embodiment.

The computer 36 according to the alternative Embodiment 2 has a processor 6d instead of the processor 6a, so it is different from the computer 6 according to the present Embodiment set forth above. Further, the processor 6d has a control element 63 instead of the control element 60, so such a point is different from the processor 6a according to the present Embodiment set forth above.

The control element 63 according to the alternative Embodiment 2 controls the speaker 5b that outputs the information sound for informing when the second imaging equipment component member 3b moves while interlocked with the first imaging equipment component member 3a. The information sound includes a warning message due to an alarm sound and a voice. In addition, according to the alternative Embodiment 2, the control element 63 may apply both the light emission element 5a and the speaker 5b to inform or only the speaker 5b without applying the light emission element 5a for informing.

Other structural elements according to the alternative Embodiment 2 are the same as the Embodiment as set forth above.

Effect of Alternative Embodiment 2

According to the alternative Embodiment 2 as set forth above, the information element 5 of the X-ray fluoroscopy imaging apparatus 300 further includes the speaker 5b that outputs the information sound. Therefore, the operator and the technician can aurally and easily understand that the second imaging equipment component member 3b moves by the information sound generated from the speaker 5b.

Further, other effects according to the alternative Embodiment 2 are the same as the aspect of the present Embodiment as set forth above.

Alternative Embodiments

In addition, the aspects of Embodiments disclosed at this time are examples and not limited thereto in any points. The scope of the present invention is specified in the claims but not in the above description of the aspect of Embodiments and all alternative (alternative examples) are included in the scope of the claims and equivalents thereof.

For example, the control element 60 controls the moves of the C-arm 30 while interlocked with the of the table 31 according to the present Embodiment and the alternative Embodiment 2 as set forth above and the move of the display unit 32 while interlocked with the move of the C-arm 30 according to the alternative Embodiment 1 as set forth above, but the present invention is not limited thereto. For example, the control element may control the moves of the display unit 32 while interlocked with the move of C-arm 30 in case of that the display unit 32 interferes the move of the C-arm 30 when the C-arm moves while interlocked with the move of the table 31. Specifically, the control element may move both the C-arm 30 and the display unit 32 while interlocked with the move of the table 31. When the control element controls both the C-arm and the move of the display unit 32 while interlocked with the move of the table 31, the information element 5 may be installed to both the C-arm 30 and the display unit 32 or both the display unit moving mechanism 7c and the C-arm moving mechanism 7b.

Further, the examples illustrate that the first imaging equipment component member 3a is the table 31 and the second imaging equipment component member 3b is C-arm 30 according to the present Embodiment and the alternative Embodiment 2 as set forth above and the first imaging equipment component member 3a is the C-arm 30 and the second imaging equipment component member 3b is the display unit 32 according to the alternative Embodiment 1, but the present invention is not limited thereto. As long as the member is intentionally moved by the operator, the first imaging equipment component member 3a can be any member of the C-arm 30, the table 31 and the display unit 32. Further, as long as the member is moved while interlocked with the move of the first imaging equipment component member 3, the second imaging equipment component member 3b can be any member of the C-arm 30, the table 31 and the display unit 32. In addition, the member that moves in a large area and is heavy is the C-arm 30 among the C-arm 30, the table 31 and the display unit 32. Accordingly, the C-arm 30 among the C-arm 30, the table 31 and the display unit 32 is most affected when the operator or the technician contacts thereto. Therefore, the information element 5 may be installed at least to the C-arm 30 or the C-arm moving mechanism 7b.

Further, the move mode in the case of moving a plurality of the imaging equipment component members 3 decides which member of the plurality of the imaging equipment component members 3 is the first imaging equipment component member 3a and which member thereof is the second imaging equipment component member 3b. Specifically, the C-arm 30, the table 31 and the display mode 32 can be either the first imaging equipment component member 3a or the second imaging equipment component member 3b in accordance with the move mode. Therefore, in the structure wherein a likelihood where the first imaging equipment component member 3a and the second imaging equipment component member 3b can be changed in accordance with the move mode selected by the operator exists, the information element 5 should be installed to all of the plurality of the imaging equipment component members 3 or the plurality of moving mechanisms 7.

Further, according to the present Embodiment, the alternative Embodiment 1 and the alternative Embodiment 2 as set forth above, the example of the single plane type wherein the C-arm 30 is one is illustrated, but the present invention is not limited thereto. For example, it can be a biplane type where there are two C-arms 30.

Further, according to the present Embodiment, the alternative Embodiment 1 and the alternative Embodiment 2 as set forth above, the example wherein the information element 5 informs when the C-arm 30 moves while interlocked with the move of the table 31, but the present invention is not limited thereto. For example, the control element may control the information element 5 for informing when the table 31 moves while interlocked with the move of the C-arm 30. Specifically, it may be acceptable as long as that the control element controls the information element 5 for informing when the second imaging equipment component member 3b moves while interlocked with the move of the first imaging equipment component 3a among the plurality of the imaging equipment component members 3. Given such a structure is provided, the operator can be informed relative to the imaging equipment component members 3 that move while interlocked therewith even when the X-ray fluoroscopic imaging apparatus 100 decides the imaging equipment component member 3 to be moved. As a result, it can be understood that which member of the imaging equipment component members 3 moving while interlocked with the predetermined imaging equipment component member 3 without depending on the understanding level of the operator relative to the equipment specification.

Further, the examples illustrate that the information element 5 is installed to the second imaging equipment component member 3b and informs that the second imaging equipment component member 3b according to the present Embodiment, the alternative Embodiment 1 and the alternative Embodiment 2 as set forth above, but the present invention is not limited thereto. For example, the structure may be configured to inform that the second imaging equipment component member 3b moves and also to install the information element 5 to the first imaging equipment component member 3a as well and then to allow the information element 5 to inform when the first imaging equipment component member 3a moves.

Further, according to the present Embodiment, the alternative Embodiment 1 and the alternative Embodiment 2 as set forth above, the example is illustrated wherein the control element decides whether the second imaging equipment component member 3b moves while interlocked with the move of the first imaging equipment component member 3a or not, but the present invention is not limited thereto. For example, the control element may not decide whether the second imaging equipment component member 3b should be moved while interlocked with the move of the first imaging equipment component member 3a or not. Specifically, the control element may control the information element 5 for informing based on the second operation input. However, when conducting informing based on the second operation input, the information element 5 may inform even when the second imaging equipment component member 3b does not move. Given the information element 5 informs the incident even when the second imaging equipment component member 3b does not move, the operator is confused. Therefore, it is desirable that control element decides whether the second imaging equipment component member 3b should be moved while interlocked with the move of the first imaging equipment component member 3a or not.

Further, according to the present Embodiment, the alternative Embodiment 1 and the alternative Embodiment 2 as set forth above, the example, wherein it is decided whether the information element 5 informs based on the present position and the target position of the second imaging equipment component member 3b, is illustrated, but the present invention is not limited thereto. For example, the control element may decide whether the information element 5 informs or not based on the first imaging equipment component member 3a and the position of the second imaging equipment component member 3b. Specifically, the control element may decide whether the information element 5 informs or not by deciding whether the second imaging equipment component member 3b should be moved or not based on the position of the first imaging equipment component member 3a and the position of the second imaging equipment component member 3b.

Further, according to the present Embodiment and the alternative Embodiments 2, the example wherein the information element 5 is installed to the moving mechanism 7 is illustrated, but the present invention is not limited thereto. The information element 5 may be installed to the second imaging equipment component member 3b. If the information in which the second imaging equipment component member 3b moves while interlocked with the move of the first imaging equipment component member 3a can be provided, the information element 5 can be installed anywhere.

Further, according to the present Embodiment and the alternative Embodiment 1, the example wherein the control element controls to provide the information as to the move of the second imaging equipment component member 3b by switching the light emission 5a from lighting-on to light flashing is illustrated, but the present invention is not limited thereto. For example, the control element may control to provide the information as to the move of the second imaging equipment component member 3b by differentiating the color of the light that the light emission element 5a outputs. As long as the information as to the move of the second imaging equipment component member 3b can be provided with the light output from the light emission element 5a, the aspect for informing is not concerned.

Further, according to the present Embodiment and the alternative Embodiment 1 as set forth above, the examples wherein the information element 5 includes the light emission element 5a and according to the alternative Embodiment 2, the information element 5 includes the speaker 5b, but the present invention is not limited thereto. For example, the information element 5 may include a monitor that displays the incident in which the second imaging equipment component member 3b moves. When the information element 5 includes the monitor, an arrow sign indicating the direction in which the second imaging equipment component member 3b is about moving can be displayed or the message of the direction in which the second imaging equipment component member 3b is about moving.

Further, according to the present Embodiment and the alternative Embodiment 2 as set forth above, the example wherein the information element 5 includes the light emission element 5a that is installed to one side and the other side of the C-arm moving mechanism 7b, but the present invention is not limited thereto. For example, one light emission element as the information element 5 may be installed to all circumference surface of the C-arm moving mechanism 7b. Further, one light emission element, as the information element 5, which protrudes on the top surface of the moving mechanism 7 may be equipped. Even when the operators are in both one side and the other side of the moving mechanism 7 and the information in which the second imaging equipment component member 3b moves while interlocked with the move of the first imaging equipment component member 3a can be provided, the positioning and number of the light emission element 5a may not be concerned.

Further, according to the present Embodiment, the alternative Embodiment 1 and the alternative Embodiment 2 as set forth above, the example wherein the control element provides the information when the second imaging equipment component member 3b is moved while interlocked with the move of the first imaging equipment component member 3a takes place to the predetermined position is illustrated, but the present invention is not limited thereto. For example, the control element may control the information element 5 to provide the informing to suppress an interference of the second imaging equipment component member 3b when the first imaging equipment component member 3a is moved to the arbitrary position and the second imaging equipment component member 3b moves.

Further, according to the present Embodiment, the alternative Embodiment 1 and the alternative Embodiment 2 as set forth above, the example wherein the operator operates the input receiving element 4 using a hand is illustrated, but the present invention is not limited thereto. For example, the input receiving element 4 that the operator operates using a foot can be i.e., a foot switch. Further, the input receiving element 4 may include both i.e., a hand switch, which the operator operates using the hand, and i.e., the foot switch, which the operator operates using a foot.

Further, according to the present Embodiment, the alternative Embodiment 1 and the alternative Embodiment 2 as set forth above, the example wherein the control element moves the first imaging equipment component member 3a and the second imaging equipment component member 3b at the same time and in parallel is illustrated, but the present invention is not limited thereto. For example, the control element may move the first imaging equipment component member 3a after moving the second imaging equipment component member 3b. Given the first operation input moves the first imaging equipment component member 3a and the second imaging equipment component member 3b, the moves can be conducted at the same time or in order.

(Aspects of the Present Invention)

The above examples of the aspects of alternative Embodiments are specific examples in accordance with the below aspects.

(Term 1)

An X-ray fluoroscopic imaging apparatus comprises: a plurality of imaging equipment component members that comprises an X-ray source that irradiates an X-ray to a subject, an X-ray detector that detects an X-ray irradiated from the X-ray ray radiation source to a subject and transmits through the subject, a C-arm that holds the X-ray source and the X-ray detector under the condition of facing each other, a table on which the subject is loaded, and a display unit that displays an X-ray image of the subject; an input receiving element that receives an operation input by an operator; an information element that informs a move of any member of the plurality of the imaging equipment component members; and a control element; wherein the control element control the information element that informs that a second imaging equipment component member moves when conducting a control of the move of a first imaging equipment component member based on a first operation input to move the first imaging equipment component member among the plurality of imaging equipment component members and another control of the move of the second imaging equipment component member different from the first imaging equipment component member of the plurality of the imaging equipment component members while interlocked with the move of the first imaging equipment component member.

(Term 2)

The X-ray fluoroscopic imaging apparatus according to the Term 1, wherein the control element controls the information element to inform in advance prior to starting the move of the first imaging equipment component member based on the first operation input when receiving an input of the move mode for moving the second imaging equipment component member while interlocked with the move of the first imaging equipment component member as the second operation input.

(Term 3)

The control element decides whether the second imaging equipment component member should be moved or not when receiving the second operation input while interlocked with the move of the first imaging equipment component member, and controls the information element to inform when the second imaging equipment component member should be moved while interlocked with the move of the first imaging equipment component member and the information element not to inform when the second imaging equipment component member should not be moved while interlocked with the move of the first imaging equipment component member.

(Term 4)

The X-ray fluoroscopic imaging apparatus according to Term 3, wherein the control element acquires the present position that is the position before the second imaging equipment component member moves and the target position that is the position after the second imaging equipment component member moves when the first imaging equipment component member is moved to the predetermined position based on the first operation input, controls the information element to inform when the present position and the target position are different, and controls the information element not to inform when the present position and the target position are the same.

(Term 5)

The X-ray fluoroscopic imaging apparatus according to Term 2 further comprises: a plurality of moving mechanisms that move at least two of the plurality of the imaging equipment component members, and the information element is installed to the second imaging equipment component member and at least one of the pluralities of moving mechanisms that moves the second imaging equipment component member among the plurality of the moving mechanisms.

(Term 6)

The X-ray fluoroscopic imaging apparatus according to Term 5, wherein the information element is installed to one side and the other side of the moving mechanism moves the second imaging equipment component member.

(Term 7)

The X-ray fluoroscopic imaging apparatus according to Term 1 further comprises: a table moving mechanism which moves the table and the C-arm moving mechanism that moves the C-arm; wherein when the control element controls the information element for informing that the C-arm moves when conducting the control of the move of the C-arm as the second imaging equipment component member by the C-arm moving mechanism while interlocked with the move of the table as the first imaging equipment component by the table moving mechanism.

(Term 8)

The X-ray fluoroscopic imaging apparatus according to Term 1 further comprises: a C-arm moving mechanism that moves the C-arm; a display unit moving mechanism that moves the display unit; wherein the control element controls the information element for informing that the display unit moves when moving the display unit by the display unit moving mechanism while interlocked with the move of the C-arm as the first imaging equipment component by the C-arm moving mechanism.

(Term 9)

The X-ray fluoroscopic imaging apparatus according to Term 1, wherein the information element includes a light emission element that informs by emitting a light.

(Term 10)

The X-ray fluoroscopic imaging apparatus according to Term 1, wherein the control element further includes a speaker that outputs an information sound.

REFERENCE OF SIGNS

1 X-ray source
2 X-ray detector
3 A plurality of imaging equipment component members 3a First imaging equipment component member
3b Second imaging equipment component member
4 Input receiving element
5 Information element
5a Light emission element
5b Speaker
7 A plurality of moving mechanisms
7a Table movement mechanism
7b C-arm moving mechanism
7c Display unit moving mechanism
10 X-ray image
30 C-arm
31 Table
32 Display unit
50, 52 Present position
51, 53 Target position
60, 62, 63 Control element
90 Subject
100, 200, 300 X-ray fluoroscopic imaging apparatus It will be further understood by those of skill in the art that the apparatus and devices and the elements herein, without limitation, and including the sub components such as operational structures, circuits, communication pathways, and related elements, control elements of all kinds, display circuits and display systems and elements, any necessary driving elements, inputs, sensors, detectors, memory elements, processors and any combinations of these structures etc. as will be understood by those of skill in the art as also being identified as or capable of operating the systems and devices and subcomponents noted herein and structures that accomplish the functions without restrictive language or label requirements since those of skill in the art are well versed in related X-Ray Fluoroscopic Imaging Systems, devices, computer and operational controls and technologies of radiographic devices and all their sub components, including various circuits and combinations of circuits without departing from the scope and spirit of the present invention.

Although only a few embodiments have been disclosed in detail above, other embodiments are possible, and the inventors intend these to be encompassed within this specification. The specification describes certain technological solutions to solve the technical problems that are described expressly and inherently in this application. This disclosure describes embodiments, and the claims are intended to cover any modification or alternative or generalization of these embodiments which might be predictable to a person having ordinary skill in the art.

Those of skill would further appreciate that the various illustrative logical blocks, modules, circuits, and algorithm steps described in connection with the embodiments disclosed herein may be implemented as electronic hardware, computer software running on one or more specific purpose machines that are programmed to carry out the operations described in this application, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the exemplary embodiments.

The various illustrative logical blocks, modules, and circuits described in connection with the embodiments disclosed herein, may be implemented or performed with a general or specific purpose processor, or with hardware that carries out these functions. A general-purpose processor may be a microprocessor, but in the alternative, the processor may be any conventional processor, controller, microcontroller, or state machine. The processor can be part of a computer system that also has an internal bus connecting to cards or other hardware, running based on a system BIOS or equivalent that contains startup and boot software, system memory which provides temporary storage for an operating system, drivers for the hardware and for application programs, disk interface which provides an interface between internal storage device(s) and the other hardware, an external peripheral controller which interfaces to external devices such as a backup storage device, and a network that connects to a hard wired network cable such as Ethernet or may be a wireless connection such as a RF link running under a wireless protocol.

A processor may also be implemented as a combination of computing devices, e.g., a combination of a DSP and a microprocessor, a plurality of microprocessors, one or more microprocessors in conjunction with a DSP core, or any other such configuration. These devices may also be used to select values for devices as described herein.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer.

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

What is claimed is:

1. An X-ray fluoroscopic imaging apparatus, comprising:
a plurality of imaging equipment component members, further comprising:
  an X-ray source that irradiates an X-ray to a subject;
  an X-ray detector that detects the X-ray irradiated from said X-ray source;
  a C-arm that holds said X-ray source and said X-ray detector while facing each other;
  a table on which said subject is loaded; and
a display unit that displays an X-ray image of said subject;
an input receiving element that receives an operation input by an operator;
an information element that informs a move of any member of said plurality of imaging equipment component members; and
a control element;
wherein said control element controls said information element to inform said information element that a second imaging equipment component member moves when conducting one control of a move of said first imaging equipment component member based on a first operation input to move said first imaging equipment component member among said plurality of imaging equipment component members and another control of said move of said second imaging equipment component member different from said first imaging equipment component member of said plurality of said imaging equipment component members while interlocked with said move of said first imaging equipment component member.

2. The X-ray fluoroscopic imaging apparatus, according to claim 1, wherein:
said control element controls said information element to inform said information element in advance prior to starting a move of said first imaging equipment component member based on said first operation input when receiving an input of a move mode for moving said second imaging equipment component member while interlocked with said move of said first imaging equipment component member as a second operation input.

3. The X-ray fluoroscopic imaging apparatus, according to claim 2, wherein:
said control element decides whether said second imaging equipment component member should be moved or not when receiving said second operation input while interlocked with said move of said first imaging equipment component member; and
said control element controls said information element to inform when said second imaging equipment component member should be moved while interlocked with said move of said first imaging equipment component member and whereas said information element not to inform when said second imaging equipment component member should not be moved while interlocked with said move of said first imaging equipment component member.

4. The X-ray fluoroscopic imaging apparatus, according to claim 3, wherein:
said control element acquires a present position that is a position before said second imaging equipment component member moves and a target position that is a position after said second imaging equipment component member moves when said first imaging equipment component member is moved to a predetermined position based on said first operation input, controls said information element to inform when said present position and said target position are different, and controls said information element not to inform when said present position and said target position are the same.

5. The X-ray fluoroscopic imaging apparatus, according to claim 2, further comprising:
a plurality of moving mechanisms that move at least two of said plurality of the imaging equipment component members; and
wherein said information element is installed to said second imaging equipment component member and at least one of moving mechanisms that move said second imaging equipment component member among said plurality of moving mechanisms.

6. The X-ray fluoroscopic imaging apparatus, according to claim 5, wherein:
said information element is installed to one side and the other side of said moving mechanism that moves said second imaging equipment component member.

7. The X-ray fluoroscopic imaging apparatus, according to claim 1, further comprising:
a table moving mechanism which moves said table and a C-arm moving mechanism that moves said C-arm; and
wherein when said control element controls said information element for informing that said C-arm moves when conducting a control of a move of said C-arm as said second imaging equipment component member by said C-arm moving mechanism while interlocked with a move of said table as said first imaging equipment component by said table moving mechanism.

8. The X-ray fluoroscopic imaging apparatus, according to claim 1, further comprising:
a C-arm moving mechanism that moves said C-arm; and
a display unit moving mechanism that moves said display unit;
wherein said control element controls said information element for informing that said display unit moves when moving said display unit as said second imaging equipment component member by said display unit moving mechanism while interlocked with a move of said C-arm as said first imaging equipment component by said C-arm moving mechanism.

9. The X-ray fluoroscopic imaging apparatus, according to claim 1, wherein:
said information element comprises a light emission element that informs by emitting a light.

10. The X-ray fluoroscopic imaging apparatus, according to claim 1, wherein:
said information element further comprises:
a speaker that outputs an information sound.

* * * * *